United States Patent
Neumann

(10) Patent No.: US 8,657,742 B2
(45) Date of Patent: Feb. 25, 2014

(54) MEDICAL MEASURING DEVICE

(75) Inventor: Rolf Neumann, Calw (DE)

(73) Assignee: Koninklijke Philips N.V., Eindhoven (NL)

( * ) Notice: Subject to any disclaimer, the term of this patent is extended or adjusted under 35 U.S.C. 154(b) by 1005 days.

(21) Appl. No.: 10/596,111

(22) PCT Filed: Nov. 23, 2004

(86) PCT No.: PCT/IB2004/052511
§ 371 (c)(1), (2), (4) Date: Mar. 6, 2007

(87) PCT Pub. No.: WO2005/053527
PCT Pub. Date: Jun. 16, 2005

(65) Prior Publication Data
US 2008/0039699 A1    Feb. 14, 2008

(30) Foreign Application Priority Data
Dec. 2, 2003  (EP) .................................... 03104501

(51) Int. Cl.
*A61B 5/00* (2006.01)
*G06F 19/00* (2011.01)
*G06F 11/07* (2006.01)

(52) U.S. Cl.
CPC ........ *G06F 19/3406* (2013.01); *G06F 11/0784* (2013.01); *A61B 5/7221* (2013.01)
USPC ...................................................... 600/301

(58) Field of Classification Search
USPC ................... 600/300–301; 128/903–905, 920
See application file for complete search history.

(56) References Cited

U.S. PATENT DOCUMENTS

| | | | |
|---|---|---|---|
| 3,449,745 A | | 6/1969 | Holt |
| 4,869,253 A | * | 9/1989 | Craig et al. ................... 600/323 |
| 5,137,458 A | * | 8/1992 | Ungs et al. .................... 434/262 |
| 5,170,791 A | | 12/1992 | Boos et al. |
| 5,247,932 A | | 9/1993 | Chung et al. |
| 5,262,944 A | | 11/1993 | Weisner et al. |
| 5,417,222 A | * | 5/1995 | Dempsey et al. ............. 600/509 |
| 5,433,209 A | | 7/1995 | Gallant et al. |
| 5,501,230 A | | 3/1996 | Laribiere |
| 5,544,661 A | | 8/1996 | Davis et al. |
| 5,620,472 A | * | 4/1997 | Rahbari .......................... 607/27 |
| 5,638,816 A | * | 6/1997 | Kiani-Azarbayjany et al. ............................. 600/316 |
| 5,704,351 A | * | 1/1998 | Mortara et al. ............... 600/382 |

(Continued)

FOREIGN PATENT DOCUMENTS

| | | |
|---|---|---|
| JP | 2001078974 A | 3/2001 |
| JP | 2002351981 A | 12/2002 |

(Continued)

*Primary Examiner* — Bill Thomson
*Assistant Examiner* — Bobby Soriano

(57) ABSTRACT

A medical measuring device or system (10) includes at least one measuring apparatus (12, 14). Each measuring apparatus, in turn, has at least one sensor (16, 18) for generating a measuring signal representing a sensed physiological parameter, e.g. ECG signals, of a patient (20, 22). The measuring apparatuses (12, 14) incorporate the measuring signal into a carrier signal which is transmitted a wireless communication route (24, 26) to a centrally located data detection device (24) which displays graphs (42) or numerical values (40) representing the sensed physiological parameters. The at least one measuring apparatus (12, 14) signals the quality of the measuring signals to a wearing patient (20) via an LED (32, 34) or loudspeaker (28, 30).

12 Claims, 1 Drawing Sheet

(56) References Cited

U.S. PATENT DOCUMENTS

| | | | | |
|---|---|---|---|---|
| 5,730,143 A | * | 3/1998 | Schwarzberg | 600/523 |
| 5,733,259 A | * | 3/1998 | Valcke et al. | 604/66 |
| 5,865,744 A | * | 2/1999 | Lemelson | 600/407 |
| 5,931,791 A | * | 8/1999 | Saltzstein et al. | 600/513 |
| 6,282,439 B1 | * | 8/2001 | Ruha | 600/509 |
| 6,282,440 B1 | * | 8/2001 | Brodnick et al. | 600/512 |
| 6,319,200 B1 | * | 11/2001 | Lai et al. | 600/300 |
| 6,364,834 B1 | * | 4/2002 | Reuss et al. | 600/300 |
| 6,415,166 B1 | | 7/2002 | Van Hoy et al. | |
| 6,449,501 B1 | | 9/2002 | Reuss | |
| 6,551,252 B2 | * | 4/2003 | Sackner et al. | 600/536 |
| 6,658,276 B2 | * | 12/2003 | Kianl et al. | 600/322 |
| 6,728,564 B2 | * | 4/2004 | Lahteenmaki | 600/383 |
| 6,811,535 B2 | * | 11/2004 | Palti et al. | 600/499 |
| 6,850,788 B2 | * | 2/2005 | Al-Ali | 600/323 |
| 6,863,652 B2 | * | 3/2005 | Huang et al. | 600/300 |
| 6,893,396 B2 | * | 5/2005 | Schulze et al. | 600/300 |
| 7,016,707 B2 | | 3/2006 | Fujisawa et al. | |
| 7,100,601 B2 | | 9/2006 | Bruna | 128/200.14 |
| 7,115,097 B2 | * | 10/2006 | Johnson | 600/538 |
| 7,174,206 B2 | * | 2/2007 | Frei et al. | 600/544 |
| 7,371,214 B2 | * | 5/2008 | Kouchi et al. | 600/300 |
| 8,187,181 B2 | * | 5/2012 | Osorio et al. | 600/300 |
| 2002/0035315 A1 | | 3/2002 | Ali et al. | |
| 2002/0109621 A1 | * | 8/2002 | Khair et al. | 341/174 |
| 2002/0161291 A1 | | 10/2002 | Kianl et al. | |
| 2003/0004403 A1 | * | 1/2003 | Drinan et al. | 600/301 |
| 2003/0023183 A1 | | 1/2003 | Williams | |
| 2003/0120164 A1 | | 6/2003 | Nielsen et al. | |
| 2003/0217747 A1 | * | 11/2003 | Hickle et al. | 128/203.12 |
| 2004/0030226 A1 | * | 2/2004 | Quy | 600/300 |
| 2004/0122295 A1 | * | 6/2004 | Hatlestad et al. | 600/300 |

FOREIGN PATENT DOCUMENTS

| | | |
|---|---|---|
| JP | 2003144394 A | 5/2003 |
| JP | 2003264632 A | 9/2003 |
| JP | 2003271732 A | 9/2003 |
| WO | WO 94/10902 A1 | 5/1994 |
| WO | 02091918 A2 | 11/2002 |
| WO | WO 03/009749 A1 | 2/2003 |

* cited by examiner

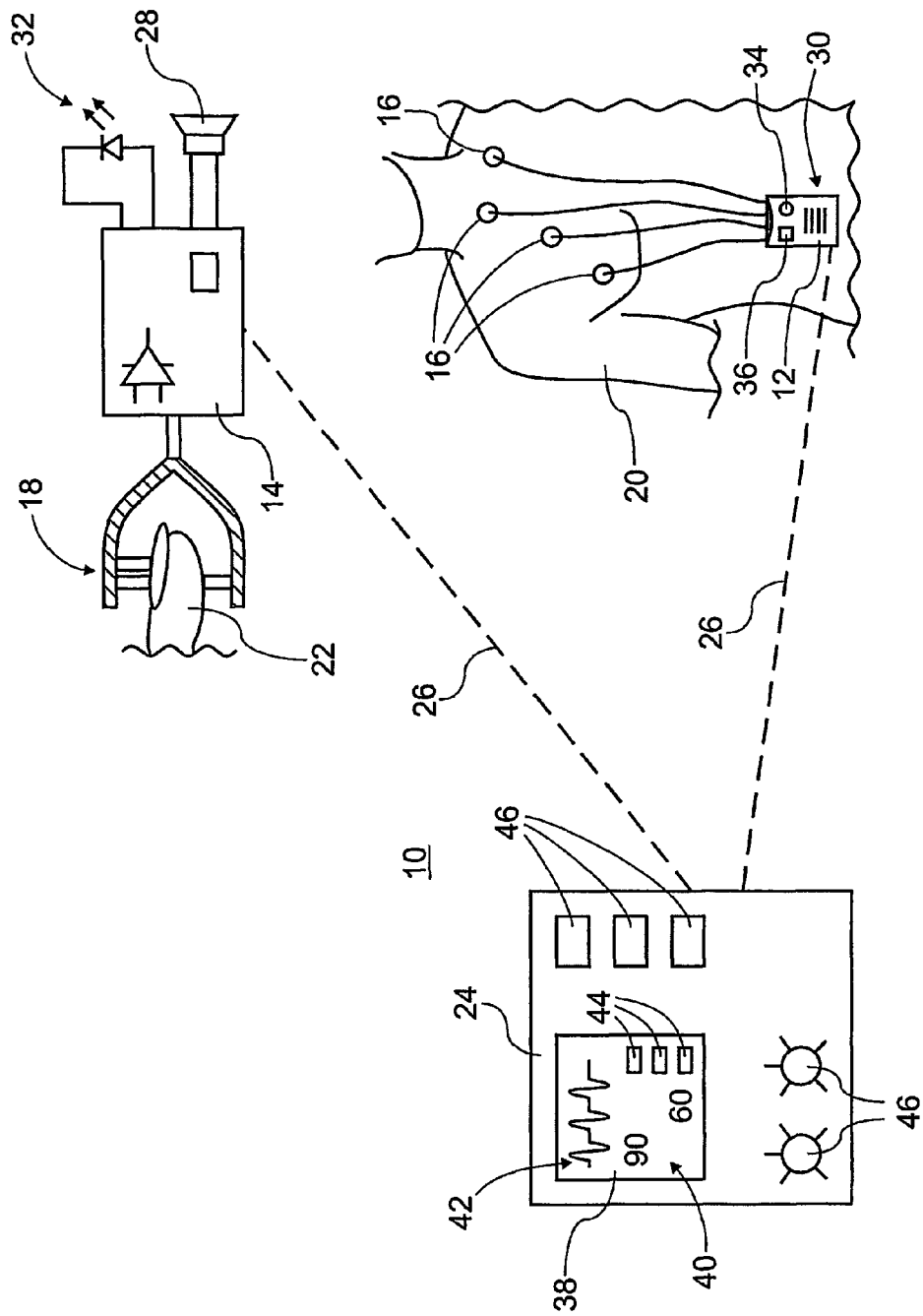

MEDICAL MEASURING DEVICE

The invention relates to a medical measuring device according to claim 1.

Instead of stationary and large measuring apparatuses, small and mobile apparatuses are used more and more frequently in the medical sector, which can be carried by patients and therefore allow greater freedom of movement. An autonomous ECG recorder is known, for example, from U.S. Pat. No. 5,433,209 and is designed as a portable apparatus allowing leads-off detection and alarm actuation on the portable apparatus which is implemented automatically according to a fixed sequence once the apparatus has been switched on.

Mobile devices of this type are generally optimized with respect to a small size and low power consumption. They therefore do not generally have detailed displays, but only small displays designed for the basic functions such as on/off or the battery status.

Devices of this type are increasingly no longer used as autonomous units, but as remote units for measuring data detection in a distributed measuring and measuring data detection system. These units then communicate with a stationary apparatus via a generally wireless communication connection, via which measuring signals are transmitted from a remote unit or a measuring apparatus to the stationary apparatus or the measuring data detection device.

However, when sensors of the remote units are placed on the body of a patient, medical staff cannot generally see a stationary apparatus with its detailed displays located in another room. Therefore they have no information about the correct placing on the body of the patient with respect to good quality of the measuring signals. For this purpose, the staff have to go to the stationary apparatus once the sensors have been placed and check the measuring signal quality. However, this is very time-consuming.

A further problem is that directly after the placing of sensors of a remote unit, the measuring signal quality is frequently very good but some time later deteriorates. It is therefore generally necessary for medical staff to check the measuring signal quality from time to time at the stationary apparatus. However, this is also very time-consuming.

An object of the present invention is therefore to propose a medical measuring device which is easier for medical staff to handle than the devices described at the outset, in particular requiring less time for monitoring.

A patient-worn measuring apparatus is described in which signal quality from a sensor, e.g., electrode, is measured directly at the measuring apparatus. Medical staff are therefore spared the time-consuming checking of the quality of the measuring signals at a central unit like the measuring data detection device.

A medical measuring device has at least one measuring apparatus which has at least one sensor for generating a measuring signal of a patient, and a measuring data detection device, which is designed to exchange the measuring signal with the at least one measuring apparatus via an, in particular, wireless communication route. The at least one measuring apparatus is designed to signal the quality of the measuring signal.

The at least one measuring apparatus is designed, in particular, to signal the quality of the measuring signal acoustically, for example by a short audio signal, when the signal quality is poor. The audio signal can thus be changed depending on the signal quality, for example it may be repeated very often in the case of very poor signal quality. Typically no audio signal is sounded when the signal quality is adequate or good.

Alternatively or in addition, the at least one measuring apparatus can be designed to signal the quality of the measuring signal optically, for example by a display with LEDs or on an LCD.

The at least one measuring device is preferably a light means with different colors, each color being associated with a predetermined range of a signal quality and activated when the quality of the measuring signal is in the corresponding, predetermined range.

The light means may also be, for example, a three-colored LED, three different colors being provided for a range of poor quality, a range of medium and a range of high quality. Red may be, for example, poor, yellow medium and green good signal quality.

The at least one measuring apparatus is preferably designed to signal the quality of the measuring signal automatically. In this case no activation of a signalization of the measuring signal quality is necessary by medical staff.

The at least one measuring apparatus may be designed, for example, to signal the quality of the measuring signal when it is placed on a patient at another measuring site. In other words, it is triggered automatically when the measuring site is changed and signals the signal quality.

In addition or also alternatively, the at least one measuring apparatus can be designed to signal the quality of the measuring signal, if a substantial change in the quality of the measuring signal is detected, for example when a patient has removed one or more sensors.

The at least one measuring apparatus can also be designed to signal the quality of the measuring signal on demand, for example by pressing a button on the measuring apparatus or by a corresponding demand from the measuring data detection device.

In a simple embodiment, the at least one measuring apparatus is designed to signal the quality of the measuring signal in such a way that falling below a predetermined signal quality is signaled. In other words there is a threshold value in the form of the predetermined signal quality. The falling below of the threshold value can be detected by a comparator in the measuring apparatus and trigger or activate signaling.

For preferred application areas in the medical sector, the at least one measuring apparatus is designed to signal the quality of the measuring signal on the basis of an evaluation of one or more parameters such as the perfusion index, transmission level, interference level, the signal form or the like.

The at least one measuring apparatus is preferably a pulsoximeter, an ECG recorder and/or ultrasound measuring head.

Further advantages of the application possibilities of the present invention emerge from the following description of an embodiment of the invention with the single drawing.

The single FIGURE of the drawing shows a medical measuring device 10 in the form of a distributed medical measuring system with measuring apparatuses 12 and 14 and a central measuring data detection device 24 which is used for storing and displaying medical measuring data and for central control of the measuring apparatus 12 and 14.

The measuring data detection device 24 comprises an LCD display screen 38 for displaying medical measuring data. The medical measuring data comprise, for example, a curve pattern 42, numerical values 40 for measuring values, or other display information 44. The measuring data detection device 24 has various operating elements 46 for adjusting measuring parameters, the display on the screen 38 and functions of this type of the measuring data detection device 24.

The measuring device 12 is a portable ECG measuring apparatus which has a plurality of ECG electrodes 16 as sensors. As shown in the FIGURE, a patient 20 carries the ECG measuring apparatus 12 on his upper body, on which the ECG electrodes 16 are fastened. The ECG measuring device 12 has an ECG recorder for recording the ECG signals picked up via the ECG sensor 16. It also comprises a radio unit, with which it can build up a radio communication connection 26 with the measuring data detection device 24 for transmitting measuring signals.

To facilitate the correct placing of the ECG electrodes 16 on the upper body of the patient 20 for medical staff, the ECG measuring apparatus 12 has a three-colored LED 34 and a loudspeaker 30. The LED 34 and the loudspeaker 30 are used for optical or acoustic signaling of the quality of measuring signals which are captured via the ECG electrodes 16.

When the ECG measuring apparatus 12 detects that no measuring signal with adequate quality can be received via the ECG electrodes 16, it switches the color of the LED 34 to red to display a poor or lesser signal quality. Furthermore, an acoustic signal in the form of a short periodic audio signal sounds over the loudspeaker 30 for as long as the signal quality is not adequate.

The signal quality is checked fully automatically in the ECG measuring apparatus 12, as soon as it is switched on. It is also possible to start a test of the signal quality by actuating a signal quality test button 36 on the ECG measuring apparatus 12. This may be carried out, for example, by the patient 20 himself. When the signal quality is adequate, the ECG measuring device 12 transmits measuring signals of the ECG electrodes 16 via the radio communication connection 26 to the measuring data detection device 24 which shows the signals received, for example in the form of the curve pattern 42 on the large LCD display screen 38 and records the course of the measuring signals.

The measuring apparatus 14 is a pulsoximeter and connected to a pulsoximeter sensor 18, in which one finger 22 of the patient is located. The measuring signals of the sensor 18 are transmitted to the pulsoximeter measuring apparatus 14. The measuring apparatus comprises a comparator for comparing the signal quality of the measuring signals received with the predetermined threshold value for a predetermined signal quality. When the signal quality received is less than the predetermined threshold value, the comparator output signal activates an LED 32 and an audio signal generator which controls the loudspeaker 28 with an audio signal. In this case, there is therefore optical and acoustic signaling that the quality of the signal of the pulsoximeter sensor 18 is not adequate to ensure reliable recording in the measuring data detection device 24.

The signal quality can then be changed by the patient or medical staff by changing the position of the pulsoximeter sensor 18 in order to receive an adequate signal quality. When the signal quality is adequate, the measuring signals are transmitted from the pulsoximeter measuring apparatus 14 via a radio communication connection 26 to the measuring data detection device 24 which displays the measuring signals received in the form of numerical values on the screen 38 and records them.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

LIST OF REFERENCE NUMERALS 10 medical measuring device
12 ECG measuring apparatus
14 pulsoximeter
16 ECG electrodes
18 pulsoximeter sensor
20 patient
22 finger of a patient
24 measuring data detection device
26 radio communication connection
28, 30 loudspeaker
32, 34 LED
36 signal quality test button
38 LCD display screen
40 numerical values
42 curve pattern
46 operating elements

The invention claimed is:

1. A medical measuring system comprising:
one or more patient body mounted sensors which contact a portion of a patient to measure physiological patient data and generate physiological patient data signals indicative of the measured physiological patient data;
a patient body mounted measuring apparatus worn by the patient, the patient body mounted measuring apparatus receives the physiological patient data signals from the one or more sensors, evaluates the measured physiological patient data signals from the one or more sensors for a change in a quality of the physiological patient data signal, and indicates the quality of the physiological patient data signals to the patient wherein the measuring apparatus evaluates the measured medical data signals for one or more of an interference level and a signal form to determine the quality of the physiological patient data signals generated by the sensors as received at the measuring apparatus; and
a measurement display apparatus detached from the patient that displays physiological patient data generated by the one or more sensors, the physiological patent data being wirelessly transferred from the patient body mounted measuring apparatus to the measurement display apparatus; and
wherein the measuring apparatus compares the determined quality with a preselected quality level and transmits the patient data wirelessly to the measurement apparatus in response to the determined quality meeting or exceeding the preselected level and signals the wearer in response to the determined quality falling below the preselected level.

2. The medical measuring system as claimed in claim 1, wherein the measuring apparatus includes an optical indicator which includes:
a light with a plurality of colors, each color being associated with one of a plurality of predetermined ranges of the at least one physiological data signal quality to indicate when the quality of the at least one physiological data measurement signal is in the corresponding one of the plurality of predetermined ranges.

3. The medical measuring system as claimed in claim 1, wherein the measuring apparatus indicates the quality of the physiological data signal in response to one of the sensors being placed on another measuring site of the patient wearing the measuring apparatus.

4. The medical measuring system as claimed in claim 1, wherein the measuring apparatus indicates the quality of physiological data signal in response to a preselected change in the quality of the physiological data signal from the sensor.

5. The medical measuring system as claimed in claim 1, wherein the at least one sensor includes a pulsoximeter, an ECG recorder or ultrasound measuring head.

6. The medical measuring system of claim 1, wherein the measuring apparatus indicates the quality of the physiological patient data signals to the patient in response to the determined quality of the physiological patient data signals being below a threshold and generates at least one of:
   an acoustic signal to the patient to which the measuring apparatus is mounted, and
   an optical signal via a light mounted on the measuring apparatus.

7. The medical measuring system of claim 1, wherein the measuring apparatus does not display the physiological patient data.

8. The medical measuring system of claim 1, wherein the quality is indicated in a manner which is humanly perceivable to the patient locally adjacent the measuring apparatus, wherein the quality is not indicated at the measurement display apparatus.

9. A medical measuring system comprising:
   a data device including a display screen for displaying at least one of medical measurement values and graphs;
   at least one sensor worn by a patient which generates at least one physiological data measurement signal indicative of physiological data of the patient;
   at least one mobile measuring apparatus worn by the patient which (1) receives the at least one physiological data measurement signal from the at least one sensor, (2) evaluates the at least one physiological data measurement signal from the at least one sensor for a change in a quality of the at least one physiological data measurement signal and indicates the quality of the at least one physiological data measurement signal generated by the at least one sensor, and (3) communicates the at least one data measurement signal wirelessly to the data device, wherein the mobile measuring apparatus evaluates a signal form of the at least one physiological data measurement signal from the at least one sensor to determine the quality of the at least one physiological data measurement signal; and
   wherein the data device is disposed remote from the patient, the wireless communication between the at least one mobile measuring apparatus and the data device enabling the patient to move freely without being tethered to the data device.

10. The medical measuring system as claimed in claim 9, wherein the at least one mobile measuring apparatus includes at least one of an acoustic indicator and an optical indicator which indicates the quality of the at least one physiological data measurement signal to a wearer of the mobile measuring apparatus.

11. The medical measuring system as claimed in claim 9, wherein the at least one measuring apparatus signals the quality of the at least one physiological data measurement signal on demand.

12. A medical measuring system comprising:
   a data device including a display screen for displaying at least one of medical measurement values and graphs;
   at least one sensor worn by the patient which generates at least one physiological data measurement signal indicative of physiological data of a patient; and
   at least one mobile measuring apparatus worn by the patient which (1) receives the at least one physiological data measurement signal from the at least one sensor, (2) automatically evaluates the at least one physiological data measurement signal to determine change in a quality of the at least one physiological data measurement signal and indicates to the patient at least one of the quality and the change in the quality of the at least one physiological data measurement signal generated by the at least one sensor, and (3) communicates the at least one data measurement signal wirelessly to the data device, wherein the mobile measuring apparatus evaluates the physiological data measurement signal based on an interference level;
   wherein the data device is disposed remote from the patient, the wireless communication between the at least one mobile measuring apparatus and the data device enabling the patient to move freely without being tethered to the data device.

\* \* \* \* \*